(12) United States Patent
Kakumanu et al.

(10) Patent No.: US 9,463,163 B2
(45) Date of Patent: Oct. 11, 2016

(54) DELAYED RELEASE PHARMACEUTICAL COMPOSITION OF MESALAMINE

(75) Inventors: Vasu Kumar Kakumanu, Guntur (IN); Anju Bansal, Gurgaon (IN); Shashikanth P. Isloor, Shimoga (IN); Vinod Kumar Arora, Gurgaon (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 73 days.

(21) Appl. No.: 13/502,194

(22) PCT Filed: Oct. 18, 2010

(86) PCT No.: PCT/IB2010/054715
§ 371 (c)(1),
(2), (4) Date: Jul. 19, 2012

(87) PCT Pub. No.: WO2011/045775
PCT Pub. Date: Apr. 21, 2011

(65) Prior Publication Data
US 2012/0282333 A1     Nov. 8, 2012

(30) Foreign Application Priority Data
Oct. 16, 2009 (IN) .......................... 2151/DEL/2009

(51) Int. Cl.
| | | |
|---|---|---|
| *A61K 9/30* | (2006.01) | |
| *A61K 9/20* | (2006.01) | |
| *A61K 9/28* | (2006.01) | |
| *A61K 31/195* | (2006.01) | |
| *A61K 9/48* | (2006.01) | |

(52) U.S. Cl.
CPC ........... *A61K 9/2054* (2013.01); *A61K 9/2846* (2013.01); *A61K 31/195* (2013.01); *A61K 9/4808* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 5,171,580 A | 12/1992 | Iamartino et al. | ............ 424/490 |
| 5,541,171 A | 7/1996 | Rhodes et al. | ............ 514/166 |
| 5,716,648 A | 2/1998 | Halskov et al. | ............ 424/682 |
| 6,551,620 B2 * | 4/2003 | Otterbeck | ............ 424/489 |
| 6,773,720 B1 | 8/2004 | Villa et al. | ............ 424/450 |
| 2006/0159749 A1 | 7/2006 | Villa et al. | ............ 424/464 |
| 2008/0279938 A1 * | 11/2008 | Cho et al. | ............ 424/470 |
| 2009/0028944 A1 | 1/2009 | Sathurappan et al. | ........ 424/482 |
| 2009/0036414 A1 | 2/2009 | Du et al. | ............ 514/166 |

FOREIGN PATENT DOCUMENTS

| | | | | |
|---|---|---|---|---|
| IN | WO 2004/087113 | * | 10/2004 | |
| IN | WO 2009/047802 | * | 4/2009 | |
| WO | WO 98/26767 | * | 6/1998 | |
| WO | WO 00/76481 | | 12/2000 | ............ A61K 9/20 |
| WO | WO 2004/087113 | | 10/2004 | ............ A61K 9/32 |
| WO | WO 2005/030173 | | 4/2005 | ............ A61K 9/16 |
| WO | WO 2009/047801 | | 4/2009 | ............ A61K 31/44 |
| WO | WO 2009/047802 | | 4/2009 | ............ A61K 9/20 |

OTHER PUBLICATIONS

Bando et al., "Relationship between drug dissolution and leaching of plasticizer for pellets coated with an aqueous Eudragit® S100:L100 dispersion", International Journal of Pharmaceutics, 323(1-2):11-17 (2006).

* cited by examiner

*Primary Examiner* — Tigabu Kassa

(57) ABSTRACT

The invention relates to a delayed release pharmaceutical composition of mesalamine comprising: a) granules comprising mesalamine or pharmaceutically acceptable salts thereof and a hydrophilic polymer; b) extragranular excipients; wherein the pharmaceutical composition is further coated with a single layer of polymer.

10 Claims, No Drawings

DELAYED RELEASE PHARMACEUTICAL COMPOSITION OF MESALAMINE

FIELD OF THE INVENTION

The present invention relates to a delayed release pharmaceutical composition of mesalamine or pharmaceutically acceptable salts thereof.

BACKGROUND OF THE INVENTION

Mesalamine, 5-aminosalicylic acid, belongs to the class of anti-inflammatory agents and is used for the treatment of mild to moderate active ulcerative colitis.

Mesalamine is commercially available in various dosage forms such as Asacol® (mesalamine 200 mg and 400 mg delayed-release tablets; Procter and Gamble, USA), Asacol® HD (mesalamine 800 mg delayed-release tablets; Procter and Gamble, USA), Pentasa® (mesalamine 400 mg extended-release capsules; Shire, USA) and Lialda® (mesalamine 1.2 g delayed release tablets; Shire, USA) for oral administration. It is also commercially available for rectal administration as an aqueous suspension or as suppositories. Of all the dosage forms available, Lialda® is the only once-a-day dosage form of mesalamine available for induction of remission in patients with ulcerative colitis.

U.S. Pat. No. 5,541,171 discloses delayed release tablets comprising mesalamine coated with a layer of an anionic copolymer of methacrylic acid which is insoluble in gastric juice and intestinal juice below pH 7 but soluble in colonic intestinal juice in sufficient amount such that the dosage form remains intact until it reaches the colon.

U.S. Pat. No. 5,716,648 discloses an oral composition that relies on pH dependent soluble coating, but also includes a pH dependent alkaline material to attempt to compensate for patients with "subnormal intestinal pH".

U.S. Pat. No. 6,773,720 discloses controlled release oral pharmaceutical compositions comprising an inner lipophilic matrix in which mesalamine is partly globulated and an outer hydrophilic matrix in which the lipophilic matrix is dispersed.

U.S. Pat. No. 5,171,580 discloses a formulation which includes a core coated with three different layers: an inner layer including an anionic polymer, an outer gastro-resistant layer and intermediate swellable layer constituted by high viscosity cellulose derivatives of high molecular weight.

U.S. Patent Application No. 2009/0028944 discloses a controlled release composition comprising mesalamine particles wherein the particles are granulated with a hydrophobic polymer and further embedded in a hydrophilic matrix.

We have now developed an alternative delayed release pharmaceutical composition of mesalamine.

SUMMARY OF THE INVENTION

In one general aspect, the present invention provides for a delayed release pharmaceutical composition of mesalamine that includes: (a) granules, which include mesalamine or pharmaceutically acceptable salts thereof and a hydrophilic polymer; and (b) extragranular excipients selected from the group consisting of hydrophilic polymers, glidants, lubricants, diluents and disintegrants; wherein the pharmaceutical composition is further coated with a single layer of polymer.

Embodiments of this aspect may include one or more of the following features. For example, the hydrophilic polymer is selected from water-soluble polymers and water-swellable polymers. The hydrophilic polymer may be present in a concentration of about 0.5% to about 15% by total weight of the composition. The composition may be in the form of a tablet or capsule.

The single layer of polymer may be an enteric polymer. Suitable enteric polymers may be cellulose acetate phthalate, hydroxypropyl methylcellulose acetate phthalate, polyvinyl acetate phthalate, hydroxy propyl phthalate, hydroxypropyl methylcellulose phthalate (HPMC phthalate), hydroxypropyl methylcellulose acetate succinate; methacrylic acid/methyl methacrylate copolymers such as Type A, Type B and mixtures thereof. For example, the enteric polymer may be a mixture of copolymer of poly(methacrylic acid, methyl methacrylate) 1:1 and poly(methacrylic acid, methyl methacrylate) 1:2. The ratio of enteric polymers may vary from 1:1 to 1:4. The coating has a thickness of from about 50 μm to 150 μm.

The pharmaceutical composition may be prepared by a process that includes the steps of:
  a) granulating mesalamine or pharmaceutically acceptable salts thereof with a hydrophilic polymer;
  b) blending the granules obtained in step a) with other pharmaceutically acceptable excipients selected from hydrophilic polymers, glidants, lubricants, diluents and disintegrants;
  c) compressing the blend into suitable sized tablets or filling into suitable sized solid dosage forms; and
  d) coating the dosage form with a single layer of polymer to obtain desired pharmaceutical composition.

DETAILED DESCRIPTION OF THE INVENTION

The term "mesalamine" as employed herein is intended to include isomers, polymorphs, solvates and hydrates of mesalamine.

The term "pharmaceutically acceptable salts" include quaternary ammonium salts, acid salts including those derived from inorganic acids, such as hydrochloric, hydrobromic, sulfuric, sulfamic, phosphoric, nitric and the like; inorganic salts including metal salts, such as sodium salt, potassium salt, cesium salt; and alkaline earth metal salts, such as calcium salt, magnesium salt; organic salts including salts prepared from organic acids, such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, ☐oluenesulphonic, methanesulfonic, ethane disulfonic, oxalic, isethionic; organic amine salts, such as triethylamine salt, pyridine salt, picoline salt, ethanolamine salt, triethanolamine salt, dicyclohexylamine salt, N,N'-dibenzylethylenediamine salt and amino acid salts such as arginate, asparginate and glutamate.

The term "pharmaceutical composition" as used herein includes solid dosage forms such as tablet, capsule, pill and the like.

Hydrophilic polymers may include water-soluble polymers as well as water-swellable polymers. Suitable examples of hydrophilic polymers include celluloses, such as carboxymethyl cellulose sodium, carboxymethyl cellulose, hydroxypropyl methylcellulose or hypromellose ("HPMC"), hydroxy propyl cellulose (HPC), polyvinyl pyrrolidones, high-molecular weight polyvinylalcohols; gums, such as natural gum, agar, agrose, sodium alginate, carrageenan, fucoidan, furcellaran, laminaran, hypnea, eucheums, gum Arabic, gum ghatti, gum karaya, gum tragacanth and locust bean gum; hydrophilic colloids, such as alginates, carbopols and polyacrylamides; other substances, such as arbinoglactan, pectin, amylopectin, gelatin, N-vinyl lactams and polysaccharides.

The total amount of hydrophilic polymer present in the composition may vary from about 0.5% to about 15% by weight of the total weight of the composition.

Polyvinylpyrrolidone or "PVP" or "povidone" is a linear polymer of 1-vinyl-2-pyrrolidone. It is available in various grades such as PVP K12, K15, K17, K25, K30, K60, K90 having mean molecular weights ranging from about 2,500 to about 1,000,000.

Carbopols or carbomers are high molecular weight polymers of acrylic acid cross-linked with polyalkenyl ethers or divinyl glycol. Depending upon the degree of cross-linking and manufacturing conditions, various grades of Carbopol are available, such as carbopol 934, 934 P, 971P, 974P, 71G, 940, 910, 941, and 1342. In tablet formulations, it is used as a dry or wet binder and as a rate controlling excipient.

Hydroxypropylmethylcellulose or "HPMC" or "hypromellose" is partly O-methylated and O-(2-hydroxypropylated) cellulose. It is available in various grades, such as K4M, K15M, K35M, K100M, K200M, K100LV, E3, E5, E6, E15 and E50 varying in viscosity and extent of substitution. In oral solid dosage forms, it is primarily used as a tablet binder, film-former, and as a matrix for use in extended-release tablet formulations.

The term "pharmaceutically acceptable excipients" as used herein includes diluents, disintegrants, lubricants, glidants, plasticizers, opacifiers, coloring agents and the like.

Examples of diluents include calcium carbonate, calcium phosphate-dibasic, calcium phosphate-tribasic, calcium sulfate, microcrystalline cellulose, silicified microcrystalline cellulose, cellulose powdered, magnesium oxide, dextrates, dextrins, dextrose, fructose, kaolin, lactitol, lactose, mannitol, sorbitol, starch, pregelatinized starch, sucrose, sugar compressible, sugar confectioners or mixtures thereof.

Examples of disintegrants include sodium starch glycolate, pregelatinized starch, powdered cellulose, crospovidone, croscarmellose sodium, colloidal silicon dioxide, microcrystalline cellulose, sodium carboxymethylcellulose and dried corn starch.

Examples of lubricants and glidants include stearic acid, magnesium stearate, calcium stearate, zinc stearate, sodium stearyl fumarate, glyceryl monostearate, glyceryl palmitostearate, hydrogenated vegetable oil, mineral oil, silicon dioxide, sodium lauryl sulfate, talc, sucrose esters of fatty acid, microcrystalline wax, yellow beeswax and white beeswax.

Suitable solvents that can be used for dispersing hydrophilic polymer or granulating mesalamine may include water, ethanol, methanol, isopropyl alcohol, or mixtures thereof.

The composition is coated with a single layer of polymer. The layer may comprise an enteric polymer. Examples of enteric polymers include cellulose acetate phthalate, hydroxypropyl methylcellulose acetate phthalate, polyvinyl acetate phthalate, hydroxy propyl phthalate, hydroxypropyl methylcellulose phthalate (HPMC phthalate), hydroxypropyl methylcellulose acetate succinate; methacrylic acid/methyl methacrylate copolymers such as Type A (Eudragit® L 100, Eudragit® L 12.5), Type B (Eudragit® S100, Eudragit® S 12.5) and mixtures thereof.

Enteric coating layer may comprise a mixture of Eudragit® S and L. Their ratios may vary from 1:1 to 1:4 (Eudragit® S:Eudragit® L) based on the desired release profile.

The target weight gain after enteric coating may vary between 5-15% by weight of uncoated composition. The coating thickness of enteric polymer may vary from 50 μm to 150 μm.

The coating composition may further include pharmaceutically acceptable excipients, such as plasticizers, opacifiers and coloring agents. Examples of plasticizers include acetylated triacetin, triethyl citrate, tributyl citrate, glycerol tributyrate, diacetylated monoglyceride, polyethylene glycols, propylene glycol, sesame oil, acetyl tributyl citrate, acetyl triethyl citrate, diethyl oxalate, diethyl phthalate, diethyl maleate, diethyl fumarate, dibutyl succinate, diethylmalonate, dioctyl phthalate, dibutyl sebacate and mixtures of these.

Examples of opacifiers include titanium dioxide, talc, calcium carbonate, behenic acid and cetyl alcohol.

Examples of coloring agents include ferric oxide red, ferric oxide yellow, Lake of Tartrazine, Allura red, Lake of Quinoline yellow and Lake of Erythrosine.

The solvents that can be used for the coating are selected from the group consisting of water, ethanol, methanol, isopropyl alcohol, dichloromethane, acetone or mixture thereof.

According to one embodiment, the present invention provides for a process for the preparation of a delayed release pharmaceutical composition of mesalamine. The process includes:
 a) granulating mesalamine or pharmaceutically acceptable salt thereof with a hydrophilic polymer;
 b) blending the granules of step a) with other pharmaceutically acceptable excipients selected from the group consisting of hydrophilic polymers, glidants, diluents and disintegrants;
 c) lubricating the granules of step b);
 d) compressing the lubricated granules of step c) or filling into suitable size dosage form; and
 e) coating the dosage form of step d) with a single layer of polymer.

According to another embodiment, the present invention provides for a process for the preparation of a delayed release pharmaceutical composition of mesalamine. The process includes the steps of:
 a) blending mesalamine or pharmaceutically acceptable salts thereof with a hydrophilic polymer;
 b) granulating the blend of step a) using a suitable solvent;
 c) blending the granules of step b) with other pharmaceutically acceptable excipients selected from the group consisting of hydrophilic polymers, glidants, diluents and disintegrants;
 d) lubricating the granules of step c);
 e) compressing the lubricated granules of step d) or filling into suitable sized dosage form; and
 f) coating the dosage form of step e) with a single layer of polymer.

According to another embodiment, the present invention provides for a process for the preparation of a delayed release pharmaceutical composition of mesalamine. The process includes the steps of:
 a) blending mesalamine or pharmaceutically acceptable salts thereof with a hydrophilic polymer;
 b) granulating the above blend using slugging or roller compaction;

c) blending the granules of step b) with other pharmaceutically acceptable excipients selected from the group consisting of hydrophilic polymers, glidants, diluents and disintegrants;
d) lubricating the blend of step c);
e) compressing the lubricated granules or filling into suitable sized dosage form; and
f) coating the dosage form of step e) with a single layer of polymer.

The following examples are representative of the invention, but are not to be construed as limiting the scope of the claims.

EXAMPLES

Example 1

| S. No | Ingredient | mg/tablet |
|---|---|---|
| | Core | |
| | Intragranular | |
| 1 | Mesalamine | 1200.0 |
| 2 | Polyvinylpyrrolidone | 48.0 |
| 3 | Purified water | q.s. |
| | Extragranular | |
| 4 | Microcrystalline cellulose | 34.0 |
| 5 | Carbopol 971P | 18.0 |
| 6. | Sodium starch glycolate | 10.0 |
| 7 | Colloidal silicon dioxide | 5.0 |
| 8 | Magnesium stearate | 5.0 |
| | Core tablet weight | 1320.0 |
| | Enteric Coating | |
| 9. | Eudragit ® L 100 | 41.3 |
| 10. | Eudragit ® S 100 | 13.8 |
| 11 | Triethyl citrate | 5.5 |
| 12 | Talc | 27.5 |
| 13. | Titanium dioxide | 1.3 |
| 14. | Ferric oxide (Red) | 3.1 |
| 15. | Purified water | q.s. |
| 16. | Isopropyl alcohol | q.s. |
| | Total tablet weight | 1412.0 |

Procedure:
1. Polyvinylpyrrolidone was dissolved in purified water.
2. Mesalamine was granulated with the solution of step 1).
3. The granules obtained from step 2) were dried and sized.
4. The dried granules of step 3) were blended with extragranular excipients.
5. The blend of step 4) was lubricated with magnesium stearate and compressed into suitable sized tablet core.

Coating
6. Eudragit® L 100 and Eudragit® S 100 were dispersed in isopropyl alcohol.
7. Titanium dioxide, ferric oxide (red) and talc were suspended in water and stirred.
8. The suspension of step 7) was added to the dispersion of step 6).
9. Triethyl citrate was added to the suspension of step 8).
10. The suspension of step 9) was stirred for 30 minutes before coating.
11. Tablets obtained from step 5) were coated with suspension of step 10) to obtain desired weight gain.

Example 2

| S. No | Ingredient | mg/tablet |
|---|---|---|
| | Core | |
| | Intragranular | |
| 1 | Mesalamine | 1200.00 |
| 2 | Hydroxypropyl methylcellulose K100LV | 48.00 |
| 3 | Purified water | q.s. |
| | Extragranular | |
| 4 | Hydroxypropyl methylcellulose K100LV | 48.00 |
| 5 | Microcrystalline cellulose | 42.00 |
| 6. | Sodium starch glycolate | 10.00 |
| 7 | Colloidal silicon dioxide | 5.00 |
| 8 | Magnesium stearate | 5.00 |
| | Core tablet weight | 1358.00 |
| | Enteric Coating | |
| 9. | Eudragit ® L 100 | 42.74 |
| 10. | Eudragit ® S 100 | 14.25 |
| 11 | Triethyl citrate | 5.70 |
| 12 | Talc | 29.32 |
| 13. | Titanium dioxide | 1.30 |
| 14. | Ferric oxide (red) | 1.75 |
| 15. | Purified water | q.s. |
| 16. | Isopropyl alcohol | q.s. |
| | Total tablet weight | 1453.06 |

Procedure:
1. Hydroxypropyl methylcellulose was dispersed in purified water to form a dispersion.
2. Mesalamine was granulated with the dispersion of step 1).
3. The granules obtained from step 2) were dried and sized.
4. The dried granules of step 3) were blended with extragranular excipients.
5. The blend of step 4) was lubricated with magnesium stearate and compressed into suitable sized tablet core.

Coating
6. Eudragit® L 100 and Eudragit® S 100 were dispersed in isopropyl alcohol.
7. Titanium dioxide, ferric oxide (red) and talc were suspended in water and stirred.
8. The suspension of step 7) was added to the dispersion of step 6).
9. Triethyl citrate was added to the suspension of step 8).
10. The suspension of step 9) was stirred for 30 minutes before coating.
11. Tablets obtained from step 5) were coated with the suspension of step 10) to obtain desired weight gain.

Dissolution Data

Mesalamine tablets of Examples 1 and 2 were subjected to an in-vitro dissolution study with the following conditions and results:

Media: 0.1N HCl for initial 2 hours, followed by pH 6.4 phosphate buffer for 1 hour and subsequently in 900 ml of phosphate buffer pH 7.2

Apparatus: USP apparatus Type-II, 100 rpm

Temperature: 37° C.±0.5° C.

TABLE 1

In-vitro dissolution data of above examples vs Lialda ® in pH 7.2 phosphate buffer after 2 hours in 0.1N HCl and 1 hour in pH 6.4 phosphate buffer

| Time (hrs) | Cumulative % Release of Mesalamine | | |
|---|---|---|---|
| | Lialda ® | Example 1 | Example 2 |
| 1 | 8 | 4 | 8 |
| 2 | 33 | 34 | 32 |
| 4 | 77 | 79 | 72 |
| 6 | 102 | 98 | 94 |

While particular embodiments and examples have been described above, it will be apparent that various modifications can be made without departing from the scope of the invention.

Example 3

| S. No | Ingredient | mg/tablet |
|---|---|---|
| | Core Intragranular | |
| 1 | Mesalamine | 800.0 |
| 2 | Hydroxypropyl methylcellulose K100LV | 12.0 |
| 3 | Purified water | q.s. |
| | Extragranular | |
| 4 | Microcrystalline cellulose | 40.0 |
| 5 | Sodium starch glycolate | 20.0 |
| 6 | Magnesium stearate | 4.0 |
| 7 | Colloidal silicon dioxide | 4.0 |
| | Core tablet weight | 880.0 |
| | Enteric Coating | |
| 8. | Eudragit ® L 100 | 26.0 |
| 9. | Eudragit ® S 100 | 8.7 |
| 10. | Triethyl citrate | 3.5 |
| 11. | Talc | 17.3 |
| 12. | Titanium dioxide | 0.7 |
| 13. | Ferric oxide (Red) | 1.2 |
| 14. | Purified water | q.s. |
| 15. | Isopropyl alcohol | q.s. |
| | Total tablet weight | 937.0 |

Procedure:
1. Hydroxypropyl methylcellulose was dispersed in purified water.
2. Mesalamine was granulated with the dispersion of step 1).
3. The granules obtained from step 2) were dried and sized.
4. The dried granules of step 3) were blended with extragranular excipients.
5. The blend of step 4) was lubricated with magnesium stearate and compressed into suitable sized tablet core.

Coating
6. Eudragit® L 100 and Eudragit® S 100 were dispersed in isopropyl alcohol.
7. Titanium dioxide, ferric oxide (red) and talc were suspended in water under stirring.
8. The suspension of step 7) was added to the dispersion of step 6).
9. Triethyl citrate was added to the suspension of step 8).
10. The suspension of step 9) was stirred for 30 minutes before coating.
11. The tablets obtained from step 5) were coated with the suspension of step 10) to obtain the desired weight gain.

Example 4

| S. No | Ingredient | mg/tablet |
|---|---|---|
| | Core Intragranular | |
| 1. | Mesalamine | 800.0 |
| 2 | Polyvinylpyrrolidone | 32.0 |
| 3 | Purified water | q.s. |
| | Extragranular | |
| 4 | Microcrystalline cellulose | 20.0 |
| 5. | Sodium starch glycolate | 20.0 |
| 6. | Colloidal silicon dioxide | 4.0 |
| 7. | Magnesium stearate | 4.0 |
| | Core tablet weight | 880.0 |
| | Enteric Coating | |
| 8. | Eudragit ® L 100 | 26.0 |
| 9. | Eudragit ® S 100 | 8.7 |
| 10. | Triethyl citrate | 3.5 |
| 11. | Talc | 17.3 |
| 12. | Titanium dioxide | 0.7 |
| 13. | Ferric oxide (Red) | 1.2 |
| 14. | Purified water | q.s. |
| 15. | Isopropyl alcohol | q.s. |
| | Total tablet weight | 937.0 |

Procedure:
1. Polyvinylpyrrolidone was dissolved in purified water.
2. Mesalamine was granulated with the solution of step 1).
3. The granules obtained from step 2) were dried and sized.
4. The dried granules of step 3) were blended with extragranular excipients.
5. The blend of step 4) were lubricated with magnesium stearate and compressed into a suitable sized tablet core.

Coating
6. Eudragit® L 100 and Eudragit® S 100 were dispersed in isopropyl alcohol.
7. Titanium dioxide, ferric oxide (red) and talc were suspended in water and stirred.
8. The suspension of step 7) was added to the dispersion of step 6).
9. Triethyl citrate was added to the suspension of step 8).
10. The suspension of step 9) was stirred for 30 minutes before coating.
11. The tablets obtained from step 5) were coated with the suspension of step 10) to obtain the desired weight gain.

Example 5

| S. No | Ingredient | mg/tablet |
|---|---|---|
| | Core Intragranular | |
| 1 | Mesalamine | 1200.0 |
| 2 | Hydroxypropyl methylcellulose K100LV | 48.00 |
| 3 | Purified water | q.s. |

-continued

| S. No | Ingredient | mg/tablet |
|---|---|---|
| | Extragranular | |
| 4 | Hydroxypropyl methylcellulose K4M | 12.00 |
| 5 | Microcrystalline cellulose | 42.00 |
| 6. | Sodium starch glycolate | 10.00 |
| 7 | Colloidal silicon dioxide | 5.00 |
| 8 | Magnesium stearate | 5.00 |
| | Core tablet weight | 1322.00 |

Procedure:
1. Hydroxypropyl methylcellulose was dispersed in purified water.
2. Mesalamine was granulated with the dispersion of step 1).
3. The granules obtained from step 2) were dried and sized.
4. The dried granules of step 3) were blended with extragranular excipients.
5. The blend of step 4) was lubricated with magnesium stearate and compressed into a suitable sized tablet core.

Example 6

| S. No | Ingredient | mg/tablet |
|---|---|---|
| | Core Intragranular | |
| 1 | Mesalamine | 1200.0 |
| 2 | Hydroxypropyl methylcellulose K100LV | 48.00 |
| 3 | Purified water | q.s. |
| | Extragranular | |
| 4 | Hydroxypropyl cellulose-H (HPC-H) | 12.00 |
| 5 | Microcrystalline cellulose | 42.00 |
| 6. | Sodium starch glycolate | 10.00 |
| 7 | Colloidal silicon dioxide | 5.00 |
| 8 | Magnesium stearate | 5.00 |
| | Core tablet weight | 1322.00 |

Procedure:
1. Hydroxypropyl methylcellulose was dispersed in purified water.
2. Mesalamine was granulated with the dispersion of step 1).
3. The granules obtained from step 2) were dried and sized.
4. The dried granules of step 3) were blended with extragranular excipients.
5. The blend of step 4) was lubricated with magnesium stearate and compressed into a suitable sized tablet core.

Example 7

| S. No | Ingredient | mg/tablet |
|---|---|---|
| | Core Intragranular | |
| 1 | Mesalamine | 1200.0 |
| 2 | Hydroxypropyl methylcellulose K100LV | 48.00 |
| 3 | Purified water | q.s. |
| | Extragranular | |
| 4 | Hydroxypropyl cellulose-M (HPC-M) | 36.00 |
| 5 | Microcrystalline cellulose | 42.00 |
| 6. | Sodium starch glycolate | 10.00 |
| 7 | Colloidal silicon dioxide | 5.00 |
| 8 | Magnesium stearate | 5.00 |
| | Core tablet weight | 1346.00 |

Procedure:
1. Hydroxypropyl methylcellulose was dispersed in purified water.
2. Mesalamine was granulated with the dispersion of step 1).
3. The granules obtained from step 2) were dried and sized.
4. The dried granules of step 3) were blended with extragranular excipients.
5. The blend of step 4) was lubricated with magnesium stearate and compressed into a suitable sized tablet core.

We claim:

1. A delayed release pharmaceutical composition of mesalamine consisting of: (a) granules, consisting of mesalamine or pharmaceutically acceptable salts thereof and a hydrophilic polymer; (b) extragranular excipients selected from the group consisting of hydrophilic polymers, glidants, lubricants, diluents and disintegrants; and (c) a single layer coating comprising at least one polymer and one or more pharmaceutically acceptable excipients.

2. The pharmaceutical composition according to claim 1, wherein the hydrophilic polymer in the granules is selected from the group consisting of water-soluble polymers and water-swellable polymers.

3. The pharmaceutical composition according to claim 2, wherein the hydrophilic polymer is present in a concentration of about 0.5% to about 15% by total weight of the composition.

4. The pharmaceutical composition according to claim 1, wherein the composition is a tablet or capsule.

5. The pharmaceutical composition according to claim 1, wherein the at least one polymer in the single layer coating comprises an enteric polymer.

6. The pharmaceutical composition according to claim 5, wherein the enteric polymer is selected from the group consisting of cellulose acetate phthalate, hydroxypropyl methylcellulose acetate phthalate, polyvinyl acetate phthalate, hydroxy propyl phthalate, hydroxypropyl methylcellulose phthalate (HPMC phthalate), hydroxypropyl methylcellulose acetate succinate; methacrylic acid/methyl methacrylate copolymers of Type A, Type B and mixtures thereof.

7. The pharmaceutical composition according to claim 6, wherein the enteric polymer is a mixture of copolymer of poly(methacrylic acid, methyl methacrylate) 1:1 and poly(methacrylic acid, methyl methacrylate) 1:2.

8. The pharmaceutical composition according to claim 7, wherein the ratio of enteric polymers may vary from 1:1 to 1:4.

9. The pharmaceutical composition according to claim 1 wherein the composition is prepared by a process comprising the steps of:
   a) granulating mesalamine or pharmaceutically acceptable salts thereof with a hydrophilic polymer;
   b) blending the granules obtained in step a) with other pharmaceutically acceptable excipients selected from the group consisting of hydrophilic polymers, glidants, lubricants, diluents, and disintegrants;
   c) compressing the blend into suitable sized tablets or filling into suitable sized solid dosage forms; and
   d) coating the dosage form with a single layer coating comprising at least one polymer and one or more pharmaceutically acceptable excipients to obtain desired pharmaceutical composition.

10. The pharmaceutical composition according to claim 1, wherein the one or more pharmaceutically acceptable excipients in the single layer coating is selected from the group consisting of plasticizers, opacifiers, and coloring agents.

\* \* \* \* \*